United States Patent [19]

Turbanti et al.

[11] Patent Number: 4,780,467
[45] Date of Patent: Oct. 25, 1988

[54] ESTERS OF N-ALKYL-NORTROPINES AND THEIR QUATERNARY DERIVATIVES HAVING ANTI-BRONCHOSPASTIC ACTIVITY, AND PHARMACEUTICAL COMPOSITIONS CONTAINING THEM

[75] Inventors: Luigi Turbanti; Guido Cerbai, Both of Pisa, Italy

[73] Assignee: Laboratori Guidotti Spa, Pisa, Italy

[21] Appl. No.: 12,476

[22] Filed: Feb. 9, 1987

[30] Foreign Application Priority Data

Feb. 11, 1986 [IT] Italy ............................... 19371 A/86

[51] Int. Cl.⁴ .................. C07D 451/06; A61K 31/46
[52] U.S. Cl. ..................................... 514/304; 546/127
[58] Field of Search ......................... 546/127; 514/304

[56] References Cited

U.S. PATENT DOCUMENTS 2,706,198  4/1955  Weijlard ..................... 546/127

*Primary Examiner*—Alan L. Rotman
*Attorney, Agent, or Firm*—Nixon & Vanderhye

[57] ABSTRACT

The esters of N-alkyl-nortropines with phenyl-cyclohexen-carboxylic and phenyl-cyclohexen-acetic acids and their quaternary ammonium derivatives with alkyl halides and alkyl sulphates having general formula:

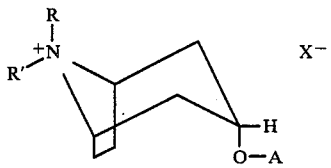

wherein when A = 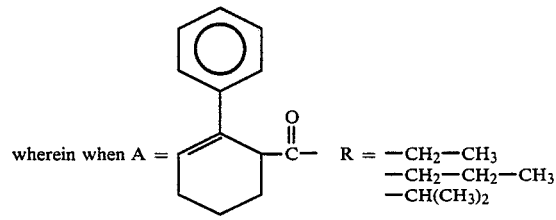 R = $-CH_2-CH_3$
$-CH_2-CH_2-CH_3$
$-CH(CH_3)_2$ and when A = 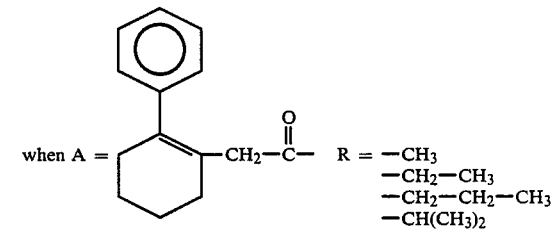 R = $-CH_3$
$-CH_2-CH_3$
$-CH_2-CH_2-CH_3$
$-CH(CH_3)_2$ whereas R'= —, $-H$, $-CH_3$, $-CH_2-CH_3$, $-CH_2-CH_2-CH_3$, $-CH(CH_3)_2$, $-CH_2-CH_2-CH_2-CH_3$, $-CH_2CH-(CH_3)_2$ $X^- = Cl, Br, I, CH_3SO_4$ show anti-bronchospastic activity. The invention relates also to the processes for their preparation and to the pharmaceutical compositions containing them.

4 Claims, No Drawings

ESTERS OF N-ALKYL-NORTROPINES AND THEIR QUATERNARY DERIVATIVES HAVING ANTI-BRONCHOSPASTIC ACTIVITY, AND PHARMACEUTICAL COMPOSITIONS CONTAINING THEM

The present invention relates to a series of novel esters of N-alkyl-nortropines with phenyl-cyclohexen-carboxylic and phenyl-cyclohexen-acetic acids and their quaternary ammonium derivatives with alkyl halides and alkyl sulphates having anti-bronchospastic activity, to processes for their preparation and to pharmaceutical compositions containing them. The products of the present invention correspond to the following general formula:

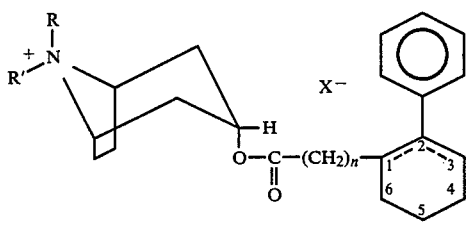

wherein
n=0, 1 (and when n=0 the double bond is in the position 1-2 and when n=1 the double bond is in the position 2-3)

$R=$—$CH_3$, —$CH_2$—$CH_3$, —$CH_2$—$CH_2$—$CH_3$, —$CH(CH_3)_2$ $R'=$—, —H, —$CH_3$, —$CH_2$—$CH_3$, —$CH_2$—$CH_2$—$CH_3$, —$CH(CH_3)_2$, —$CH_2$—$CH_2$—$CH_2$—$CH_3$—, —$CH_2$—$CH_2$—$(CH_3)_2$ $X^-=Cl, Br, I, CH_3SO_4$

R being —$CH_3$ only if n—1

More precisely the compounds of the present invention comprise a series of esters of N-ethyl, N-isopropyl-, N-propyl-nortropine with 2-phenyl-2-cyclohexen-1-carboxylic and 2-phenyl-1-cyclohexen-1-acetic acid, also the ester of the latter with tropine being included, and the related quaternary ammonium derivatives with alkyl halides and alkyl sulphates, as it results from the general formula I.

The compounds of the invention, particularly the quaternary ammonium derivatives, are endowed with a remarkable anti-bronchospastic action which is revealed both in the in vitro tests and in the animal in vivo after administration by venous and inhalatory route, mainly with respect to the spasms induced by muscarinic agonists.

By combining these properties with the fact that this quaternary ammonium derivatives are very poorly absorbed by the gastroenteric tract and by the broncho-pulmonary one and that they are not capable of passing the hemato-encephalic barrier, the compounds of the invention are consequently efficacious pharmacologic agents used in the therapy of the broncho-obstructive forms, particularly suitable for the administration by inhalatory route, and practically devoid of side effects of atropinic type or of secondary pharmacological actions.

The interest of the compounds of the invention in the aforesaid therapy is nowadays enhanced by the almost unanimous acknowledgment of the prevailing rôole plaid by the vagous nerve in the bronchial hyperactivity (Gross and Skorodin, Am. Rev. Resp. Dis, 129, 856, 1984).

The use of atropinic derivatives an anti-bronchospastic drugs has been discovered again in the latter years also owing to a renewed interest for the whole class of antimuscarinic compounds which lead to introduce other chemical modification in the structure of the natural alkaloids, atropine and scopolamine: thus novel N-alkyl-nortropines and N-alkyl-nor-scopolamines have been developed as well as the related quaternary ammonium derivatives, among which some compounds have been selected and developed as anti-bronchospastic agents, such as ipratropium bromide (Arzneim. Forsch., 23, 468, 1973; Postgrad. Medic. J., 51, Suppl. 7, 82-4, 1975) and oxitropium bromide (Arzneim. Forsch., 35, 217, 1985: ibidem, 35, 435), both having been firstly studied as gastric anti-secretion compounds (Arzneim. Forsch., 23, 1334; ibidem 26, 960; ididem 26, 974) and described in two respective patents although being not claimed (U.S. Pat. Nos. 3,505,337 and 2,472,861).

The compounds of the present invention are distinguished with respect to the aforesaid compounds firstly under the chemical point of view, since esters of phenyl-cyclohexen-carboxylic or phenyl-cyclohexen-acetic acids are involved, namely compounds which are chemically different from the structure of the natural alkaloids.

The esterification of these acids with N-alkyl-nortropines and the subsequent quaternarization of the tertiary bases with several alkyl halides or alkyl sulphates permitted a wide class of compounds to be provided, having remarkable spasmolytic properties with respect to the tracheobronchial tract. These pharmacological properties had not been revealed in a series of basic esters of 2-phenyl-2-cyclohexen-1-carboxylic acid previously disclosed as spasmolytic agents for the gastrointestinal apparatus (U.K. Pat. No. 1194280 and U.S. Pat. No. 3,699,109).

From the pharmacological point of view the compounds of the invention show an inhibitory action against the spasms of the smooth tracheo-bronchial muscles as induced by muscarinic agents, which is particularly powerful and long lasting in some of them. Moreover some compounds are characterized with respect to the anti bronchospastic agents of anti-muscarinic type by being active even against the bronchospams as induced by PAF-acether, which is a powerful mediator of the bronchial asthma recently identified, and the importance of which being more and more evidenced (Page et al., TIPS, 5, 239, 1984; Morely et al., Lancet ii, 1142, 1984). By this action they are qualitatively distinguished over the standard anti-muscarinic compounds, which have no activity with respect to the PAF-acether induced bronchospasm.

Object of the present invention are also the processes for the preparation of this class of compounds consisting in reacting, as shown in the scheme 1, the derivative of an acid selected among 2-phenyl-2-cyclohexen-1-carboxylic and 2-phenyl-1-cyclohexen-1-acetic acid, suitable to promote a reaction of nucleophylic substitution at the acyl carbon atom, such as an acid chloride or an alkyl ester, with a basic alcohol selected in the group comprising tropine, N-ethyl-nortropine, N-isopropyl-nortropine, N-propyl-nortropine, having in the alcoholic hydroxyl the nucleophylic group capable of bonding the acyl carbon atom. Such a reaction is carried out in an aprotic solvent, either in the presence or not of an acid acceptor, by isolating from the reaction solvent by means of the standard proceedings, the tertiary aminoesters 5, by purifing them as bases through fractionated distillation under vacuum or as salts with hydrogen halides by crystallization, and lastly by converting these basic esters by treatment with the suitable alkyl halides or alkyl sulphates to the corresponding quaternary ammonium derivatives which are obtained as chrystalline products by isolating them from the reaction mixture after separation by cooling or by adding suitable solvent.

In the scheme 1 there is illustrated the case in which in formula 1 n=0, but the reaction scheme remains unchanged even for n=1, namely starting from the compound 3a:

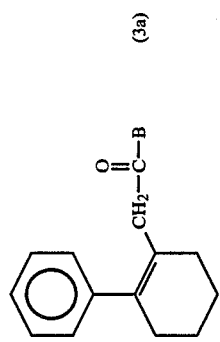
(3a)
SCHEME I
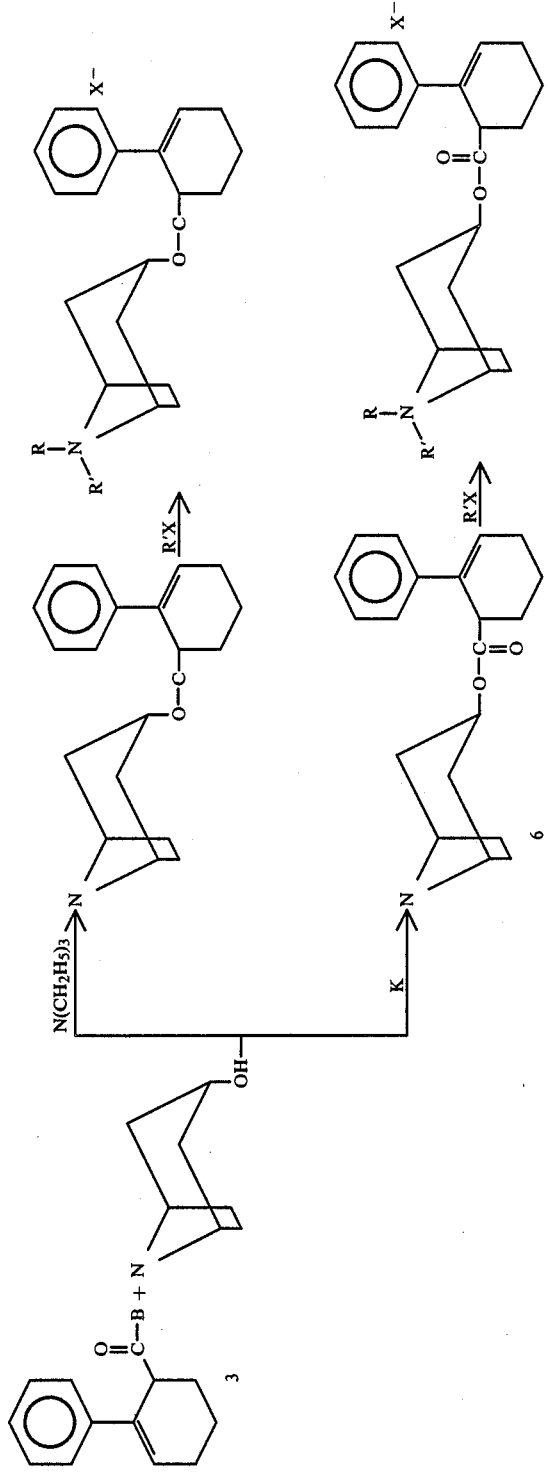

wherein Q=—Cl, —OCH₃ e R, R' and X have the above indicated meanings.

The intermediate N-alkyl-nortropines prepared according to known processes have the endo configuration indicated by the formula 4 and are chemically defined as endo-8-alkyl-8-azabicyclo-[3.2.1]-octane-3-ols. The esterification of these azabicyclo octaneols under the experimental conditions detailedly described in the examples 2, 4, 5, 6 and 7 lead to the formation of the basic esters of formula 5 having to endo configuration.

If, on the contrary, the esterification is carried out by previously treating the N-alkyl-nortropines with metal potassium and in suitable solvents, according to the conditions described in the example 3, a mixture of the tropinic and pseudotropinic esters is obtained, namely of the endo and eso forms, from which the eso isomer of formula 6 has been obtained.

The quaternarization of the tertiary N of the esters of formula 5 and also of those of formula 6 leads to the formation of the quaternary ammonium derivatives of formula 2 and 2a indicating that the attack of the alkyl group at the nitrogen atom takes place in stereospecific manner in equatorial position.

The configuration of the tertiary basic esters (5 and 6) and of their quaternary ammonium derivatives (1 and 2a) have been demonstrated by spectrum analysis: they correspond, according to what has been reported in the literature about the synthesis of like compounds, to the indicated steric formulae.

The 2-phenyl-2-cyclohexen-1-carboxylic acid has been prepared according to the process of the U.S. Pat. No. 3,699,109 whereas the 2-phenyl-1-cyclohexen-1-acetic acid disclosed in J. Chem. Soc. 1936, 71, has been prepared by synthesis according to the known method. Also the N-alkyl-nortropines have been prepared by synthesis according to the method described in the literature (Le Roy, Keagle, Hartung; J. Am. Chem. Soc., 68, 1608–10, 1946).

The compounds of the invention have been pharmacologically studied by means of in vitro and in vivo tests, suitable to evidence the anti-bronchospastic properties of the compounds. It has been found that the quaternary ammonium derivatives show in vitro a powerful action relaxing the spasm of the trachea as induced by methacolin, which action is generally more intense by several magnetude orders with respect to the tertiary basic amminoesters. To this action a remarkable antibronchospastic action in the tests in vivo corresponded after administration by i.v. and inhalatory route. Moreover, differently from the available anti-muscarinic anti-bronchospastic compounds, some compounds as above indicated namely the more active in the two indicated tests, demonstrated also an intense activity in inhibiting the bronchospams as induced by PAF-acether and other biological actions of PAF-acether possibly related to the rôle of ths asthma mediator.

The power of some terms of the series may be expressed by the comparison values of some experimental parameters reported in the following table 1; (see Eur. Journal of Pharm. 126, 81, 1986) for the most active compound the activity of relaxing the contraction of the isolated trachea of guinea pig, as induced by methacoline, expressed as IC50 is comprised between values of the order of between $1,1 \times 10^{-9}$M and $3.0 \times 10^{-11}$M in comparison with the IC50 of $6.9 \times 10^{-9}$ and $2.0 \times 10^{-9}$M: of atropine and ipratropium bromide.

The experimental values of activity inhibiting the bronchospasm as induced by acethyl choline aerosol in the awake guinea pig expressed as ED50 are reported in table 2 (see Eur. Journal of Pharm. 126, 81, 1986) and are of between 8 and 57 nmol kg$^{-1}$ i.v. in comparison with a ED50 values of 68 and 12 nmol kg$^{-1}$ respectively of atropine and ipratropium bromide.

Moreover the property by which the compounds of the present invention are definitely distinguished over the antibronchospastic compounds already known of antimuscarinic type, is their inhibiting action against the bronchospasm as induced by PAF-acether. The experimental values of the inhibiting action of some compounds of the invention is shown in table 3. (see Agent and Action 19, page 246, 1986, Subissi A.).

The most powerful compound in this sense, the compound of example 21, in fact inhibits the bronchospasm induced by PAF-acether in the anestetized guinea pig with a ED$_{50}$ of 0.8 μmol.kg$^{-1}$ whereas atropine and ipratropium bromide are fully inactive up to 3 μmol/kg.

Table 4, inturn, shows the acute toxicity of the compounds of table 3.

TABLE 1

Isolated trachea of guinea pig precontracted with methacoline (IC$_{50}$M)

| General Formula | R | R' = — | R' = —CH$_3$ | R' = —CH$_2$—CH$_3$ | R' = —CH—CH$_3$ \| CH$_3$ | R' = —CH$_2$—CH$_2$—CH$_3$ | R' = —CH$_2$—CH—CH$_3$ \| CH$_3$ | R' = —CH$_2$—(CH$_2$)$_2$—CH$_3$ |
|---|---|---|---|---|---|---|---|---|
| [structure: phenyl-cyclohexenyl-bicyclic-N(R)(R')-O, X = J] | —CH$_2$—CH$_3$ | $2.8 \times 10^{-7}$ | $9.5 \times 10^{-10}$ | $3.0 \times 10^{-11}$ | $6.3 \times 10^{-7}$ | $7.0 \times 10^{-8}$ | $5.4 \times 10^{-8}$ | $6.9 \times 10^{-8}$ |
| | —CH—CH$_3$ \| CH$_3$ | $3.5 \times 10^{-7}$ | $6.7 \times 10^{-10}$ | $5.0 \times 10^{-10}$ | $4.6 \times 10^{-8}$ | $8.7 \times 10^{-8}$ | $8.0 \times 10^{-8}$ | $4.5 \times 10^{-8}$ |
| | —CH$_2$—CH$_2$—CH$_3$ | $1.7 \times 10^{-6}$ | $3.3 \times 10^{-9}$ | $1.2 \times 10^{-8}$ | $4.9 \times 10^{-7}$ | $3.8 \times 10^{-7}$ | $1.2 \times 10^{-6}$ | $1.9 \times 10^{-7}$ |
| [structure: phenyl-cyclohexenyl-bicyclic-N(R)(R')-O-C(=O)-CH$_2$, X = J] | —CH$_3$ | $4.2 \times 10^{-6}$ | $1.1 \times 10^{-9}$ | $3.2 \times 10^{-8}$ | $4.5 \times 10^{-8}$ | $2.4 \times 10^{-7}$ | | |
| | —CH—CH$_3$ \| CH$_3$ | $3.0 \times 10^{-5}$ | $2.7 \times 10^{-6}$ | $9.0 \times 10^{-6}$ | $6.7 \times 10^{-5}$ | $8.5 \times 10^{-6}$ | | |
| Atropine sulphate | | $6.9 \times 10^{-9}$ | | | | | | |
| Ipratropim bromide | | $2.0 \times 10^{-9}$ | | | | | | |

TABLE 2

Inhibition of bronchospasm induced by acetyl choline aerosol in guinea pig (ED$_{50}$ nmol kg$^{-1}$ i.v.)

| General Formula | R | R' = — | R' = —CH$_3$ | R' = —CH$_2$—CH$_3$ | R' = —CH—CH$_3$ \| CH$_3$ | R' = —CH$_2$—CH$_2$—CH$_3$ | R' = —CH$_2$—CH—CH$_3$ \| CH$_3$ | R' = —CH$_2$—(CH$_2$)$_2$—CH$_3$ |
|---|---|---|---|---|---|---|---|---|
| (cyclohexenyl-phenyl tropanyl ether) | —CH$_2$—CH$_3$ | 6120 | 21 | 29 | ~5900 | ~2000 | >5700 | |
| | —CH—CH$_3$ \| CH$_3$ | ~1500 | 27 | 22 | 2500 | 1500 | 1080 | 990 |
| | —CH$_2$—CH$_2$—CH | >7700 | 56 | 228 | >5700 | 2400 | >5600 | >5600 |
| (cyclohexenyl-phenyl tropanyl ester) | —CH$_3$ | ~15000 | 57 | ~400 | >600 | >600 | | |
| | —CH—CH$_3$ \| CH$_3$ | >7400 | 255 | >5700 | >5600 | >5600 | | |
| Atropine sulphate | | 68 | | | | | | |
| Ipratropime bromide | | 12 | | | | | | |

TABLE 3

| | Inhibition of PAF-acether induced bronchospasm | | | | |
|---|---|---|---|---|---|
| | PAF-acether induced bronchospasm in guinea pig - i.v. administration at the dose of | | Platelet aggregation (rabbit prp) from | | |
| Compounds Example No. | 0.3 μmol kg$^{-1}$ | 3 μmol kg$^{-1}$ | PAF acether | collagen | arachidonic acid |
| | inhibition % | | IC$_{50}$ μM | | |
| 13 | 0 | 28 ± 13 | 39.1 | >>100 | >>100 |
| 14 | 0 | 42 ± 14 | 29.9 | >>100 | >>100 |
| 20 | 3 ± 11 | 36 ± 17 | 7.7 | >>100 | >>100 |
| 21 | 43 ± 16 | 64 ± 16 | 2.4 | >>100 | >>100 |
| 25 | — | — | — | | |
| 8 | — | — | — | | |
| atropine sulphate | — | 0 | >1000 | — | ~1000 |
| ipratropime bromide | — | 7 ± 10 | >1000 | >1000 | >1000 |

TABLE 4

| | Acute toxicity | | |
|---|---|---|---|
| Compounds example n. | approximate value of LD$_{50}$ (mg kg$^{-1}$) in the mouse | | |
| | i.p. | os | os/i.p. |
| 13 | 123 | 500 | 4.1 |
| 14 | 91 | 300 | 3.3 |
| 20 | 126 | 350 | 2.8 |
| 21 | 107 | 800 | 7.5 |
| 25 | 124 | 600 | 4.8 |
| 8 | 45 | 800 | 18.0 |
| atroprine sulphate | 208 | 500 | 2.4 |
| Ipratropime bromide | 85 | 600 | 7.1 |

Such a compound furthermore inhibits some other biological actions of PAF-acether possibly related with the rôle of this asthma mediator. These pharmacological results, in combination with the poor absorption of the quaternary ammonium derivatives in the gastrointestinal and broncho-pulmonary tracts give place for the compounds of the invention to a very advantageous pharmaco-toxicologic and pharmacokinetic profile by which they are proposed as useful agent in the therapy of the broncho-obstructive form, suitable for the administration by inhalatory route and practically devoid of side effects.

The compounds of the present invention, the processes for their preparation and the pharmaceutical formulations for their therapeutical use are described in the following examples having illustrating but non limiting title.

EXAMPLE 1

Endo-3-(2-phenyl-2-cyclohexen-1-carbonyloxy)-8-sin-isopropyl-8-azabicyclo-[3.2.1]-octane (formula 5 with R=—CH(CH$_3$)$_2$)

A solution of 6.5 g (0.038 moles) of endo-8-isopropyl-8-azabyciclo-[3.2.1]-octan-3-ol and 3.87 g (0.038 moles) of triethylamine in 77 ml of 1,2-dichloroethane heated at 35° C. is added dropwise under stirring with a solution of 8.37 g (0.038 moles) of 2-phenyl-2-cyclohexen-carboxylic acid chloride.

Upon the chloride addition is completed, the temperature of the external bath is brought to 90° C. and the heating of the reaction mixture is continued under stirring for 20 hours. The reaction mixture is left to cool to room temperature, then maintained at rest in refrigerator at 0° C. for about 12 hours. By filtration under vacuum a crystalline precipitate is collected, which is washed on the filter with ether and dried. The residue consists of about 80% of the theoretical weight of trietilamine hydrochloride formed during the reaction. The filtrate is then evaporated to dryness under vacuum and the oily residue is treated with 80 ml of ether. The ether suspension obtained is extracted with 50 ml of 10% diluted HCl and the acidic aqueous solution is treated under stirring with portions of NaHCO$_3$, up to complete neutralization. The resulting suspension is extracted with several portions of ether and the ether extracts are combined, dehydrated over anhydrous Na$_2$SO$_4$ and evaporated under vacuum. The oily residue (8.9 g) is distilled under vacuum by collecting the fraction boiling at 171° C. at 0.2 mm Hg. There are obtained 8.22 g (yield 60.6%) of unitary aminoester having purity degree of ≧98% (GLC, CSS). The structure is confirmed through elemental analysis and NMR spectrum, demonstrating the presence of only the isomer with endo configuration. The hydrochloride salt (as prepared by precipitation of the ether solution of the base treated with gaseous HCl) melts at 196° C. (from isopropanol).

EXAMPLE 2

Endo-3-(2-phenyl-2-cyclohexen-1-carbonyloxy)-8-sin-isopropyl-8-azabicyclo[3.2.1.]-octane (Formula 5 with R=—CH(CH$_3$)$_2$)

A reaction vessel, having mechanical stirrer and connected to a distillator, is charged, in the order, with 7 g (0.032 moles) of methyl 2-phenyl-2-cyclohexen-1-carboxylate, 22 mg of CH$_3$ONa (0.4 mmoles) as freshly prepared and 4 g (0.0236 moles) of N-isopropyl-nortropine. Under continous stirring, the reaction mixture, in form of a homogeneous suspension is gradually heated to 140° C. it being maintained at a pressure of 35-40 mm Hg. After 10 hours heating, the reaction mixture is taken with 40 ml toluene and the resulting suspension is filtered under vacuum to recover the unreacted N-isopropyl-nortropine. The toluene filtrate is extracted with 25 ml of 10% HCl and the acid aqueous extract is neutralized with a saturated NaHCO$_3$ solution and extracted with 20 ml dichloromethane. After dehydratation and evaporation under vacuum of the organic solution the desired aminoester is obtained with a purity greater then 98%.

EXAMPLE 3

Eso-3-(2-phenyl-2-cyclohexen-1-carbonyloxy)-8-sin-isopropyl-8-azabicyclo-[3.2.1.]-octane (Formula 6 with R=—CH(CH$_3$)$_2$)

A suspension of 1.15 g (0.0068 moles) of endo-8-isopropyl-8-azabicyclo-[3.2.1.]-octan-3-ol and 0.27 g (0.0069 g.atoms) of metal potassium in 18 ml toluene is maintained under stirring at 110° C. for 8 hours under nitrogen atmosphere, up to the formation of the potassium salt of the aminoalcohol is completed. At that point the reaction mixture is cooled to room temperature and the suspension, extremely cooled with ice and under stirring, is added with a solution of 1.49 g of 2-phenyl-2-cyclohexen-1-carboxylic acid chloride in 5 ml toluene.

The suspension is refluxed at 120° C. under stirring for 5 hours. The inorganic precipitate is removed by filtration and the toluene filtrate is vacuum evaporated so as to obtain an oily residue which is purified by dissolving in ether, extracting with 10% diluted HCl, neutralizing of the aqueous solution with $NaHCO_3$ and extracting again with ether of the obtained dense oil.

1.1 g (yield 45%) of unitary aminoester are obtained in form of dense oil boiling at 165° C. at 0.05 mmHg (analysis GLC and CSS), which is identified through elemental and chemico-physical analysis (IR and NMR spectra) as the eso form of the desired aminoester.

EXAMPLE 4

Endo-3-(2-phenyl-2-cyclohexen-1-carbonyloxy)-8-sin-ethyl-8-azabicyclo-[3.2.1.]-octane (Formula 5 with R=—$CH_2$—$CH_3$)

This compound has been prepared starting from 1.5 g (0.01 moles) of endo-8-ethyl-8-azabicyclo-[3.2.1.]-octan-3-ol, 1.01 g (0.01 moles) of triethylamine and 2.25 g (0.01 moles) of 2-phenyl-2-cyclohexen-1-carboxylic acid chloride in 25 ml of 1,2-dichloroethane, according to the process described in the example 1. The product obtained by evaporation of the ether extract can not be vacuum distilled, differently from the example 1, owing to the decomposition and is thus purified by repeated conversion into the hydrochloride salt, a glassy solid, and subsequent return to the base with $NaHCO_3$ until the aminoester, which is a dense oil, is not analytically pure (GLC, CSS). The structure and configuration have been confirmed through elemental analysis and NMR spectrum. The yield of pure final product (title ≧98%) is 58.7% m.p. (hydrochloride): 161°–162° C. (from isopropanol)

EXAMPLE 5

Endo-3-(2-phenyl-2-cyclohexen-1-carbonyloxy)-8-sin-propyl-8-azabicyclo-[3.2.1.]-octane (Formula 5 with R=—$CH_2$—$CH_2$—$CH_3$)

It is prepared, according to the process described in the example 1, from 4.3 g (0.25 moles) of endo-8-propyl-8-azabicyclo-[3.2.1.]-octan-3-ol, 2.52 g (0.025 moles) of triethylamine and 5.50 g (0.025 moles) of 2-phenyl-2-cyclohexen-1-carboxylic acid chloride in 65 ml of 1.2-dichloroethane.

The purification of the final compound is carried out through the precipitation from the ether solution of the basic aminoester by treatment with gaseous HCl of the hydrochloride which is crystallized from isopropanol. By displacement in aqueous solution with $NaHCO_3$ and extraction with ether the desired pure aminoester, (elemental analysis, GLC and CSS), is obtained in form of a resinous oil, with a yield of 47%, the configuration has been demonstrated through IR and NMR spectra. The crystalline hydrochloride (from isopropanol) melts at 158° C.

EXAMPLE 6

Endo-3-(2-phenyl-1-cyclohexen-1-acetoxy)-8-sin-methyl-8-azabicyclo-[3.2.1.]-octane (Formula 1 with n=1, R=—$CH_3$, R'=X=—)

It is prepared, according to the process described in the example 1, from 5.5 g (0.039 moles) of endo-8-methyl-8-azabicyclo-[3.2.1.]-octan-3-ole, 3.95 g (0.039 moles) of triethylamine and 13.8 g (0.039 moles) of 2-phenyl-1-cyclohexen-1-acetic acid chloride in 188 ml of 1.2-dichloroethane. The reaction raw product is purified by distillation collecting the fraction boiling at 176°–178° C. at 0.1 mmHg. 9 g of oil (yield 68%) have been obtained corresponding to the desired compound (GLC, CSS and elemental analysis); the configuration has been confirmed through the NMR spectrum.

EXAMPLE 7

Endo-3-(2-phenyl-1-cyclohexen-1-acetoxy)-8-sin-isopropyl-8-azabicyclo-[3.2.1.]-octane (Formula 1 with n=1, R=—$CH(CH_3)_2$, R'=—, X=—)

It is prepared, according to the process described in the example 1, from 2.5 g (0.015 moles) of endo-8-isopropyl-8-azabicyclo-[3.2.1.]-octan-3-ol, 1.52 g (0.15 moles) of triethylamine and 5.3 g (0.015 moles) of 2-phenyl-1-cyclohexen-1-acetic acid chloride in 25 ml of 1,2-dichloroethane. The desired aminoester is obtained in form of a crystalline solid product melting at 84° C. (from hexane), with a yield of 54%. Purity, structure and configuration have been confirmed through GLC, CSS, elemental analysis and IR and NRM spectra. The hydrochloride, precipitating from the ether solution of the base treated with anhydrous gaseous HCl melts at 205° C. (from isopropanol).

EXAMPLE 8

Endo-3-(2-phenyl-1-cyclohexen-1-acetoxy)-8,8-dimethyl-8-azoniabicyclo-[3.2.1.]-octane iodide.

(Formula 1 with n=1, R=R'=—$CH_3$, X=J)

4 g (11.78 mmoles) of endo-3-2-phenyl-1-cyclohexen-1-acetoxy-8-sin-methyl-8-azabicyclo-[3.2.1.]-octane, (example 6) are dissolved in 20 ml acetonitrile, treated with 9.2 g (4 ml) of methyl iodide (64.2 mmoles) and the resulting solution is heated to 50° C. in a closed vessel for 10 hours. By cooling a crystalline solid is spontaneously precipitated and is collected by filtration, washed on the filter with ether and purified by crystallization from methanol up to a constant melting point of 253° C. The desired product, pure, is obtained with a yield of 76%. The structure has been confirmed by elemental analysis and IR and NMR spectra.

EXAMPLE 9

Endo-3-(2-phenyl-1-cyclohexen-1-acetoxy)-8-sin-methyl-8-ethyl-8-azoniabicyclo-[3.2.1.]-octane iodide (Formula 1 with n=1, R=—$CH_3$, R'=—$C_2H_5$, X=J)

It is prepared according to example 8 from endo-3-(2-phenyl-1-cyclohexen-1-acetoxy)-8-sin-methyl-8-azabicyclo-[3.2.1.]-octane and ethyliodide, giving place to a crystalline product melting at 196° C. (from ethanol). The structure has been confirmed by elemental analysis and by IR and NMR spectra.

EXAMPLE 10

Endo-3-(2-phenyl-1-cyclohexen-1-acetoxy)-8-sin-methyl-8-propyl-8-azoniabicyclo-[3.2.1.]-octane iodide (Formula 1 with n=1, R=—$CH_3$, R'=—$CH_2$—$CH_3$, X=J).

It is prepared according to example 8 from endo-3-(2-phenyl-1-cyclohexen-1-acetoxy)-8-sin-methyl-8- azabicyclo-[3.2.1.]-octane and ethyl iodide, giving place to a crystalline product melting at 194° C. (from isopropanol). The structure is confirmed by the elemental analysis and by the IR and NMR spectra.

EXAMPLE 11

Endo-3-(2-phenyl-1-cyclohexen-1-acetoxy)-8-sin-methyl-8-isopropyl-8-azoniabicyclo-[3.2.1.]-octane iodide (Formula 1 with n=1, R=—CH$_3$, R'=—CH(CH$_3$)$_2$, X=J)

It is prepared according to example 8 from endo-3-(2-phenyl-1-cyclohexen-1-acetoxy)-8-sin-methyl-8-azabicyclo-[3.2.1.]-octane and isopropyl iodide, giving place to a crystalline product melting at 228° C. (from isopropanol).

The structure is confirmed by elemental analysis and IR and NRM spectra.

EXAMPLE 12

Eso-3-(2-phenyl-2-cyclohexen-1-carbonyloxy)-8-sin-isopropyl-8-methyl-8-azoniabicyclo-[3.2.1.]-octane iodide (Formula 2a; R=—CH(CH$_3$)$_2$, R'=—CH$_3$, X=J)

It is prepared according to example 8 from eso-3-(2-phenyl-1-cyclohexen-1-carbonyloxy)-8-sin-isopropyl-8-azabicyclo-[3.2.1.]-octane and methyl iodide, giving place to a crystalline solid melting at 213° C. (from isopropanol). The structure is confirmed by elemental analysis and IR and NMR spectra.

EXAMPLE 13

Endo-3-(2-phenyl-2-cyclohexen-1-carbonyloxy)-8-sin-isopropyl-8-methyl-8-azoniabicyclo-[3.2.1.]-octane iodide (Formula 2 with: R=—CH(CH$_3$)$_2$, R'=—CH$_3$, X=J).

It is prepared according to example 8 from endo-3-(2-phenyl-2-cyclohexen-1-carbonyloxy)-8-sin-isopropyl-8-azabicyclo-[3.2.1.]-octane and methyl iodide, giving place to a crystalline solid melting at 237° C. (from isopropanol). The structure is confirmed by the elemental analysis and the IR and NRM spectra.

EXAMPLE 14

Endo-3-(2-phenyl-2-cyclohexen-1-carbonyloxy)-8-sin-isopropyl-8-ethyl-8-azoniabicylo-[3.2.1.]-octane iodide (Formula 2 with: R=—CH(CH$_3$)$_2$, R'=—CH$_2$—CH$_3$, X=J)

It is prepared according to example 8 from endo-3-(2-phenyl-2-cyclohexen-1-carbonyloxy)-8-sin-isopropyl-8-azabicyclo-[3.2.1.]-octane and ethyl iodide giving place to a crystalline solid melting at 232°-232, 5° C. (from absolute ethanol). The structure is confirmed by elemental analysis and IR and NMR spectra.

EXAMPLE 15

Endo-3-(2-phenyl-2-cyclohexen-1-carbonyloxy)-8-sin-isopropyl-8-propyl-8-azoniabicyclo-[3.2.1.]-octane iodide (Formula 2 with: R=—CH(CH$_3$)$_2$, R'=—CH$_2$—CH$_2$—CH$_3$, X=J)

0.6 g (1.7 mmoles) of endo-3-(2-phenyl-2-cyclohexen-1-carbonyloxy)-8-sin-isopropyl-8-azabicyclo-[3.2.1.]-octane (example 1) are dissolved in 3 ml of propyl alcohol and treated with 0.58 g (3.4 mmoles) of n-propyl iodide. The resulting solution is heated in closed vessel to 80° C. for 15 hours. After cooling to room temperature, the reaction mixture is maintained at rest at 0° C. for 12 hours, during which a crystalline precipitate is formed which is collected by vacuum filtration. The filtrate is evaporated to dryness under vacuum and the oily residue (0.3 g; 0.85 mmoles) is dissolved in 2 ml of propanol treated with 0.29 g (1.7 mmoles) of n-propyl iodide and heated as above for 24 hours. After cooling and keeping at rest at 0° C. for 24 hours, a second portion of a precipitate is obtained which is collected and combined with the first one. The thus obtained product is recrystallized from n-propyl alcohol and 0.42 g (47%) of crystalline product are obtained melting at 177° C. The elemental and chemical-physical analysis (CSS and NMR spectra) confirmed the structure and the configuration of the product.

EXAMPLE 16

Endo-3-(2-phenyl-2-cyclohexen-1-carbonloxy)-8,8-di-isopropyl-8-azoniabicyclo-[3.2.1.]-octane iodide (Formula 2 with: R=R'=—CH(CH$_3$)$_2$, X=J)

It is prepared according to example 8 from endo-3-(2-phenyl-2-cyclohexen-1-carbonyloxy)-8-sin-isoproyl-8-azobicyclo-[3.2.1.]-octane and isopropyl iodide, giving place to a crystalline solid melting at 175°-177, 5° C. (from isopropanol). The structure is confirmed by elemental analysis and by IR and NMR spectra.

EXAMPLE 17

Endo-3-(2-phenyl-2-cyclohexen-1-carbonyloxy)-8-sin-isopropyl-8-n.butyl-8-azoniabicyclo-[3.2.1.]-octane iodide (Formula 2 with: R=—CH(CH$_3$)$_2$, R'=—CH$_2$—CH$_2$—CH$_2$—CH$_3$, X=J)

It is prepared according to example 8 from endo-3-(2-phenyl-2-cyclohexen-1-carbonyloxy)-8-sin-isopropyl-8-azabicyclo-[3.2.1.]-octane and n.butyl iodide, giving place to a crystalline solid melting at 184° C. (from acetonitrile). The structure is confirmed by elemental analysis and IR and NMR spectra.

EXAMPLE 18

Endo-3-(2-phenyl-2-cyclohexen-1-carbonyloxy)-8-sin-isopropyl-8-iso-butyl-8-azoniabicyclo-[3.2.1.]-octane iodide.

(Formula 2 with R=—CH(CH$_3$)$_2$, R'=—CH$_2$—CH(CH$_3$)$_2$, X=J)

It is prepared according to example 8 from endo-3-(2-phenyl-2-cyclohexen-1-carbonyloxy)-8-sin-isopropyl-8-azabicyclo-[3.2.1.]-octane and isobutyl iodide, giving place to a crystalline solid melting at 166° C. (from acetonitrile). The structure is confirmed by elemental analysis and IR and NMR spectra.

EXAMPLE 19

Endo-3-(2-phenyl-2-cyclohexen-1-carbonyloxy)-8-sin-isopropyl-8-cyclopropyl-8-azonibicyclo-[3.2.1.]-octane bromide (Formula 2 with: R=—CH(CH$_3$)$_2$, R' = 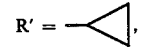, X=Br)

It is prepared according to example 8 from endo-3-(2-phenyl-2-cyclohexen-1-carbonyloxy)-8-sin-isopropyl-8- azabicyclo-[3.2.1.]-octane and cyclopropyl bromide, giving a crystalline solid melting at 193°-195° C. (from acetonitrile/ether 1:1). The structure is confirmed by elemental analysis and IR and NMR spectra.

EXAMPLE 20

Endo-3-(2-phenyl-2-cyclohexen-1-carbonyloxy)-8-sin-ethyl-8-methyl-8-azoniabicyclo-[3.2.1.]-octane iodide (Formula 2 with: R=—$CH_2$—$CH_3$, R'=—$CH_3$, X=J)

It is prepared according to example 2 from endo-3-(2-phenyl-2-cyclohexen-1-carbonyloxy)-8-sin-ethyl-8-azabicyclo-[3.2.1.]-octane and methyl iodide, giving a crystalline solid melting at 219° C. (from acetonitrile). The structure is confirmed by elemental analysis and IR and NMR spectra.

EXAMPLE 21

Endo-3-(2-phenyl-2-cyclohexene-1-carbonyloxy)-8,8-di-ethyl-azoniabicyclo-[3.2.1.]-octane iodide.

(Formula 2 with R=—$CH_2$—$CH_3$, R'=—$CH_2$—$CH_3$, X=J)

It is prepared according to example 8 from endo-3-(2-phenyl-2-cyclohexen-1-carbonyloxy)-8-sin-ethyl-8-azabicyclo-[3.2.1.]-octane and ethyl iodide, giving a crystalline solid melting at 238° C. (from acetonitrile). The structure is confirmed by elemental analysis and IR and NMR spectra.

EXAMPLE 22

Endo-3-(2-phenyl-2-cyclohexen-1-carbonyloxy)-8-sin-ethyl-8-n.propyl-8-azoniabicyclo-[3.2.1.]-octane iodide (Formula 2 with: R=—$CH_2$—$CH_3$, R'=—$CH_2$—$CH_2$—$CH_3$, X=J)

It is prepared according to example 15 from endo-3-(2-phenyl-2-cyclohexen-1-carbonyloxy)-8-sin-ethyl-azabicyclo-[3.2.1.]-octane and n-propyl iodide, giving a crystalline solid melting at 178° C. (from n.propanol). The structure is confirmed by elemental analysis and IR and NMR spectra.

EXAMPLE 23

Endo-3-(2-phenyl-2-cyclohexen-1-carbonyloxy)-8-sin-ethyl-8-isopropyl-8-azoniabicyclo-[3.2.1.]-octane iodide (Formula 2 with: R=—$CH_2$—$CH_3$, R'=—$(CH(CH_3)_2$, X=J)

It is prepared according to example 8 from endo-3-(2-phenyl-2-cyclohexen-1-carbonyloxy)-8-sin-ethyl-8-azabicyclo-[3.2.1.]-octane and isopropyl iodide, giving a solid melting at 183°-185° C. (from isopropanol). The structure is confirmed by elemental analysis and IR and NMR spectra.

EXAMPLE 24

Endo-3-(2-phenyl-2-cyclohexen-1-carbonyloxy)-8-sin-ethyl-8-isopropyl-8-azoniabicyclo-[3.2.1.]-octane iodide (Formula 2 with: R=—$CH_2$—$CH_3$, R'=—$CH_2$—$(CH_3)_2$, X=J)

It is prepared according to example 8 from endo-3-(2-phenyl-2-cyclohexen-1-carbonyloxy)-8-sin-ethyl-8-azabicyclo-[3.2.1.]-octane and isopropyl iodide, giving a crystalline solid melting aat 184°-186° C. (from isopropanol). The structure is confirmed by elemental analysis and IR and NMR spectra.

EXAMPLE 25

Endo-3-(2-phenyl-2-cyclohexen-1-carbonyloxy)-8-sin-propyl-8-methyl-8-azoniabicyclo-[3.2.1.]-octane iodide (Formula 2 with: R=—$CH_2$—$CH_2$—$CH_3$, R'=—$CH_3$, X=J)

It is prepared according to example 8 from endo-3-(2-phenyl-2-cyclohexen-1-carbonyloxy)-8-sin-propyl-8-azabicyclo-[3.2.1.]-ocane and methyl iodide, giving a solid melting at 227° C. (from isopropanol). The structure is confirmed by elemental analysis and IR and NMR spectra.

EXAMPLE 26

Endo-3-(2-phenyl-2-cyclohexen-1-carbonyloxy)-8-sin-propyl-8-ethyl-8-azoniabicyclo-[3.2.1.]-octane iodide (Formula 2 with: R=—$CH_2$—$CH_2$—$CH_3$, R'=—$CH_2$—$CH_3$, X=J)

It is prepared according to example 8 from endo-3-(2-phenyl-2-cyclohexen-1-carbonyloxy)-8-sin-propyl-8-azabicyclo-[3.2.1.]-octane and ethyl iodide, giving a solid melting at 172°-174° C. (from acetonitrile). The structure is confirmed by elemental analysis and IR and NMR spectra.

EXAMPLE 27

Endo-3-(2-phenyl-2-cyclohexen-1-carbonyloxy)-8,8-azoniabicyclo-[3.2.1.]-octane iodide (Formula 2 with: R=—$CH_2$—$CH_2$—$CH_3$, R'=—$CH_2$—$CH_2$—$CH_3$ X=J)

It is prepared according to example 8 from endo-3-(2-phenyl-2-cyclohexen-1-carbonyloxy)-8-sin-propyl-8-azabicyclo-[3.2.1.]-octane and n.-propyl iodide, giving a crystalline solid melting at 165°-166° C. (from acetonitrile). The structure is confirmed by elemental analysis and IR and NMR spectra.

EXAMPLE 28

Endo-3-(2-phenyl-2-cyclohexen-1-carbonyloxy)-8-sin-propyl-8-isopropyl-8-azoniabicyclo-[3.2.1.]-octane iodide (Formula 2 with: R=—$CH_2$—$CH_2$—$CH_3$, R'=—$CH(CH_3)_2$, X=J)

It is prepared according to example 8 from endo-3-(2-phenyl-2-cyclohexen-1-carbonyloxy)-8-sin-propyl-8-azabicyclo-[3.2.1.]-octane and isopropyl iodide, giving a crystalline solid melting at 168°-170° C. (from acetonitrile). The structure is confirmed by elemental analysis and IR and NRM spectra.

EXAMPLE 29

Endo-3-(2-phenyl-2-cyclohexen-1-carbonyloxy)-8-sin-propyl-8-n.butyl-8-azoniabicyclo-[3.2.1.]-octane iodide (Formula 2 with: R=—$CH_2$—$CH_2$—$CH_3$, R'=—$CH_2$—$CH_2$—$CH_2$—$CH_3$, X=J)

It is prepared according to example 8 from endo-3-(2-phenyl-2-cyclohexen-1-carbonyloxy)-8-sin-propyl-8-azabicycle-[3.2.1.]-octane and n.butyl iodide, giving a solid melting at 187° C. (from acetonitrile). The structure is confirmed by elemental analysis and IR and NRM spectra.

EXAMPLE 30

Endo-3-(2-phenyl-2-cyclohexen-1-carbonyloxy)-8-sin-propyl-8-isobutyl-8-azoniabicyclo-[3.2.1.]-octane iodide.

(Formula 2 with: $R=-CH_2-CH_2-CH_3$, $R'=-CH_2-CH(CH_3)_2$, $X=J$)

It is prepared according to example 8 from endo-3-(2-phenyl-2-cyclohexen-1-carbonyloxy)-8-sin-propyl-8-azabicyclo-[3.2.1.]-octane and isobutyl iodide, giving a solid melting at 153°–155° C. (from isopropanol). The structure is confirmed by elemental analysis and IR and NMR spectra.

EXAMPLE 31

Endo-3-(2-phenyl-1-cyclohexen-1-acetoxy)-8-sin-isopropyl-8-methyl-8-azoniabicyclo-[3.2.1.]-octane iodide (Formula 1 with: n=1, $R=-CH(CH_3)_2$, $R'=-CH_3$, $X=J$)

It is prepared according to example 8 from endo-3-(2-phenyl-1-cyclohexen-1-acetoxy)-8-sin-isopropyl-8-azabicyclo-[3.2.1.]-octane and methyl iodide, giving a crystalline solid melting at 248°–250° C. (from methanol). The structure is confirmed by elemental analysis and IR and NMR spectra.

EXAMPLE 32

Endo-3-(2-phenyl-1-cyclohexen-1-acetoxy)-8-sin-isopropyl-8-ethyl-8-azoniabicyclo-[3.2.1.]-octane iodide (Formula 1 with n=1, $R=-CH(CH_3)_2$, $R'=-CH_2-CH_3$, $X=J$)

It is prepared according to example 8 from endo-3-(2-phenyl-1-cyclohexen-1-acetoxy)-8-sin-isopropyl-8-azabicyclo-[3.2.1.]-octane and ethyl iodide, giving a crystalline solid melting at 256°–259° C. (from ethanol). The structure is confirmed by elemental analysis and IR and NMR spectra.

EXAMPLE 33

Endo-3-(2-phenyl-1-cyclohexen-1-acetoxy)-8-sin-isopropyl-8-propyl-8-azoniabicyclo-[3.2.1.]-octane iodide (Formula 1 with n=1, $R=-CH(CH_3)_2$, $R'=-CH_2-CH_2-CH_3$, $X=J$)

It is prepared according to example 15 starting from endo-3-(2-phenyl-1-cyclohexen-1-acetoxy)-8-sin-isopropyl-8-azabicyclo-[3.2.1.]-octane and n-propyl iodide, giving a crystalline solid melting at 249° C. (from n.propanol). The structure is confirmed by elemental analysis and IR and NMR spectra.

EXAMPLE 34

Endo-3-(2-phenyl-1-cyclohexen-1-acetoxy)-8,8-di-isopropyl-8-azoniabicyclo-[3.2.1.]-octane iodide (Formula 1 with n=1, $R=-CH(CH_3)_2$, $R'=-CH(CH_3)_2$, $X=J$)

It is prepared according to example 8 from endo-3-(2-phenyl-1-cyclohexen-1-acetoxy)-8-sin-isopropyl-8-azabicyclo-[3.2.1.]-octane and isopropyl iodide, giving a crystalline solid melting at 248° C. (from isopropanol). The structure is confirmed by elemental analysis and IR and NMR spectra.

EXAMPLE 35

Endo-3-(2-phenyl-2-cyclohexen-1-carbonyloxy)-8-sin-ethyl-8-methyl-8-azonibicyclo-[3.2.1.]-octane methylsulphate (Formula 2 with $R=-CH_2-CH_3$, $R'=R'=-CH_3$, $X=-CH_3SO_4$)

A solution of 0.72 g (2.12 mmoles) of the basic amino-ester of example 4 in 2 ml benzene is treated at room temperature with 0.504 g (0.38 ml) of dimethyl sulphate (4 mmoles). The mixture is maintained at rest at room temperature for 12 hours, during which, starting from the second hour, a crystalline product precipitates, which, upon being collected and purified by crystallization from benzene, is in form of colorless crystals, with melting point of 129° C. (with decomposition). The structure is confirmed by elemental analysis and IR and NMR spectra.

EXAMPLE 36

Endo-3-(2-phenyl-2-cyclohexen-1-carbonyloxy)-8,8-dimethyl-8-azoniabicyclo-[3.2.1.]-octane methylsulphate (Formula 2 with: $R=-CH_3$, $R'=-CH_3$, $X=-CH_3SO_4$)

It is prepared according to example 35, starting from endo-3-(2-phenyl-2-cyclohexen-1-carbonyloxy)-8-sin-methyl-8-azabicyclo-[3.2.1.]-octane and dimethylsulphate, giving a crystalline, straw-yellow solid, melting at 220° C. (from benzene). The structure is confirmed by elemental analysis and IR and NMR spectra.

EXAMPLE 37

Endo-3-(2-phenyl-2-cyclohexen-1-carbonyloxy)-8-sin-isopropyl-8-sin-isopropyl-8-methyl-8-azoniabicyclo-[3.2.1.]-octane methylsulphate (Formula 2 with: $R=-CH(CH_3)_2$, $R'=-CH_3$, $X=-CH_3SO_4$)

It is prepared according to example 35, starting from endo-3-(2-phenylcyclohexen-1-carbonyloxy)-8-sin-isopropyl-8-azabicyclo-[3.2.1.]-octane and dimethylsulphate. It is a crystalline solid melting at 132° C. from benzene. The elemental analysis corresponds to the structure looked for.

EXAMPLE 38

Endo-3-(2-phenyl-2-cyclohexen-1-carbonyloxy)-sin-propyl-8-methyl-8-azoniabicyclo-[3.2.1.]-octane methylsulphate.

(Formula 2 with: $R=-CH_2-CH_2-CH_3$, $R'=-CH_3$, $X=-CH_3SO_4$)

It is prepared according to example 35, starting from endo-3-(2-phenyl-2-cyclohexen-1-carbonyloxy)-8-sin-propyl-8-azabicyclo-[3.2.1.]-octane and dimethylsulphate. It is a crystalline solid, melting (with decomposition) at 121°–123° C. (from benzene). The elemental analysis corresponds to the structure foreseen.

EXAMPLE 39

Endo-3-(2-phenyl-2-cyclohexene-1-carbonyloxy)-8-sin-isopropyl-8-methyl-8-azoniabicyclo-[3.2.1.]-octane bromide (Formula 2 with: $R=-CH(CH_3)_2$, $R'=-CH_3$, $X=Br$)

It is prepared according to example 8 from endo-3-(2-phenyl-2-cyclohexen-1-carbonyloxy)-8-sin-isopropyl-8-azabicyclo-[3.2.1.]-octane and methyl bromide; a crystalline solid is obtained melting at 262° C. (from ethanol). The structure is confirmed by the elemental analysis and by the IR and NMR spectra.

EXAMPLE 40

Endo-3-(2-phenyl-2-cyclohexen-1-carbonyloxy)-8-sin-isopropyl-8-ethyl-8-azoniabicylo-[3.2.1.]-octane bromide (Formula 2 with: R=—CH(CH$_3$)$_2$, R'=—CH$_2$—CH$_3$, X=Br)

It is prepared according to example 8 from endo-3-(2-phenyl-2-cyclohexen-1-carbonyloxy)-8-sin-isopropyl-8-azabicyclo-[3.2.1.]-octane and ethyl bromide; a crystalline solid is obtained melting at 182°–183° C. (from absolute ethanol). The structure is confirmed through elemental analysis and IR and NMR spectra.

EXAMPLE 41

Endo-3-(2-phenyl-2-cyclohexen-1-carbonyloxy)-8-sin-ethyl-8-methyl-8-azoniabicylo-[3.2.1.]-octane bromide (Formula 2 with: R=—CH$_2$—CH$_3$, R'=—CH$_3$, X=Br)

It is prepared according to example 8 from endo-3-(2-phenyl-2-cyclohexen-1-carbonyloxy)-8-sin-ethyl-8-azabicyclo-[3.2.1.]-octane and methyl bromide; a crystalline solid is obtained melting at 226°–228° C. (from ethanol). The structure is confirmed through elemental analysis.

EXAMPLE 42

Endo-3-(2-phenyl-2-cyclohexen-1-carbonyloxy)-8,8-diethyl-8-azoniabicyclo-[3.2.1.]-octane bromide (Formula 2 with: R=—CH$_2$—CH$_3$, R'=—CH$_2$—CH$_3$, X=Br)

It is prepared according to example 8 from endo-3-(2-phenyl-2-cyclohexen-1-carbonyloxy)-8-sin-ethyl-8-azabicyclo-[3.2.1.]-octane and ethyl bromide; a crystalline solid is obtained melting at 198° C. (from ethanol). The structure is confirmed through elemental analysis and the IR and NMR spectra.

EXAMPLE 43

Example of a pharmaceutical composition suitable for the administration by inhalatory route of advisable doses of the compound of the invention.

| Compound of the example 21 | mg | 12 |
|---|---|---|
| sorbitantrioleate (Arlacel 85) | mg | 3 |
| Freon 11 | mg | 5235 |
| Freon 12 | mg | 15750 |
| Total | mg | 21000 |

Such a pharmaceutical preparation, contained in anatomizing device provided with dosing valve, permits the administration of single measured doses from 20 to 40 μg of active ingredient. Like pharmaceutical compositions can be prepared with the other compounds of the invention.

The daily posology for the therapeutical use is of 2 to 3 sprays, each of an unitary dose, 3 to 4 times a day.

The compounds of the invention may be administered to humans in dosage amounts of from 10 to 80 mg, preferably 20 to 40 mg, two to four times daily.

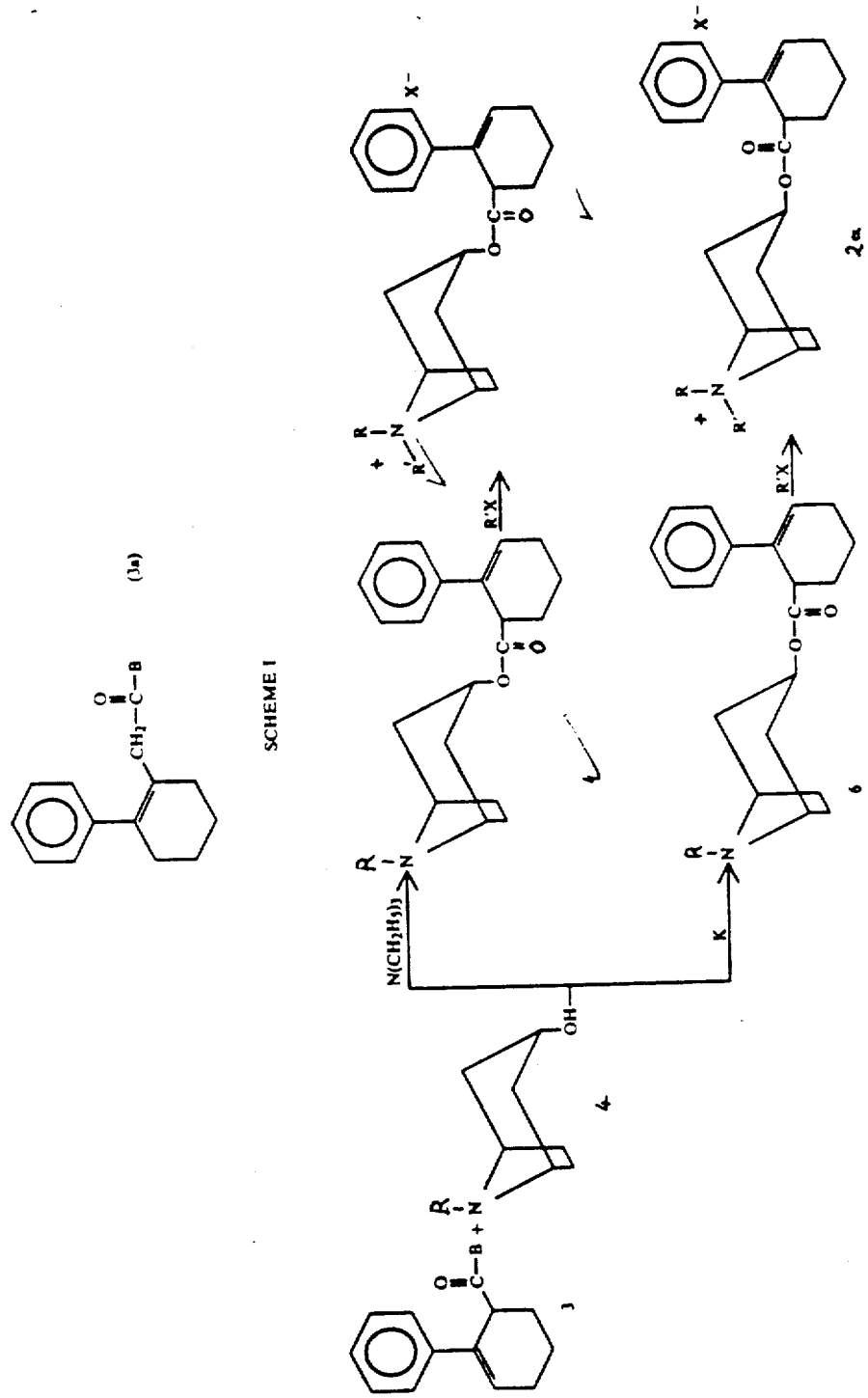

We claim:
1. A compound of the formula:

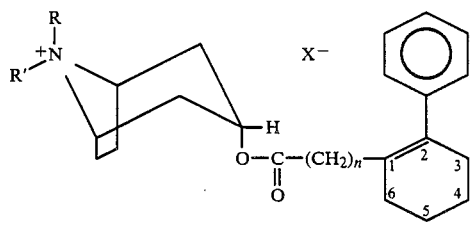

wherein
n is 0,
R is —CH$_2$—CH$_3$, —CH$_2$—CH$_2$—CH$_3$ or —CH(CH$_3$)$_2$
R' is —H, —CH$_3$, —CH$_2$CH$_3$, —CH$_2$—CH$_2$—CH$_3$, —CH(CH$_3$)$_2$, or —CH$_2$—CH$_2$—CH$_2$—CH$_3$, and
X is Cl, Br, I, CH$_3$SO$_4$.

2. A compound of claim 1, selected from the group consisting of:

Endo-3-(2-phenyl-2-cyclohexen-1-carbonyloxy)-8-sin-isopropyl-8-azabicyclo-[3.2.1.]-octane Eso-3-(2-phenyl-2-cyclohexen-1-carbonyloxy)-8-sin-isopropyl-8-azabicyclo-[3.2.1.]-octane Endo-3-(2-phenyl-2-cyclohexen-1-carbonyloxy)-8-sin-ethyl-8-azabicyclo-[3.2.1.]-octane Endo-3-(2-phenyl-2-cyclohexen-1-carbonyloxy)-8-sin-propyl-8-azabicyclo-[3.2.1.]-octane Eso-3-(2-phenyl-2-cyclohexen-1-carbonyloxy)-8-sin-isopropyl-8-sin-isopropyl-8-methyl-8-azoniabicyclo-[3.2.1.]-octane iodide Endo-3-(2-phenyl-1-cyclohexen-1-carbonyloxy)-8-sin-isopropyl-8-ethyl-8-azoniabicyclo-[3.2.1.]-octane iodide Endo-3-(2-phenyl-2-cyclohexen-1-carbonyloxy)-8-sin-isopropyl-8-ethyl-8-azoniabicyclo-[3.2.1.]-octane iodide Endo-3-(2-phenyl-1-cyclohexen-1-carbonyloxy)-8-sin-isopropyl-8-propyl-8-azoniabicyclo-[3.2.1.]-octane iodide Endo-3-(2-phenyl-2-cyclohexen-1-carbonyloxy)-8-diisopropyl-8-azoniabicyclo-[3.2.1.]-octane iodide Endo-3-(2-phenyl-2-cyclohexen-1-carbonyloxy)-8-sin-isopropyl-8-n.butyl-8-azoniabicyclo-[3.2.1.]-octane iodide Endo-3-(2-phenyl-2-cyclohexen-1-carbonyloxy)-8-sin-isopropyl-8-iso-butyl-8-azoniabicyclo-[3.2.1.]-octane iodide Endo-3-(2-phenyl-2-cyclohexen-1-carbonyloxy)-8-sin-isopropyl-8-cyclopropyl-8-azoniabicyclo-[3.2.1.]-octane bromide Endo-3-(2-phenyl-2-cyclohexen-1-carbonyloxy)-8-sin-ethyl-8-methyl-8-azoniabicyclo-[3.2.1.]-octane iodide Endo-3-(2-phenyl-2-cyclohexen-1-carbonyloxy)-8,8-diethyl-8-azoniabicyclo-[3.2.1.]-octane iodide Endo-3-(2-phenyl-2-cyclohexen-1-carbonyloxy)-8-sin-ethyl-8-n-propyl-8-azoniabicyclo-[3.2.1.]-octane iodide Endo-3-(2-phenyl-2-cyclohexen-1-carbonyloxy)-8-sin-ethyl-8-isopropyl-8-azoniabicyclo-[3.2.1.]-octane iodide Endo-3-(2-phenyl-2-cyclohexen-1-carbonyloxy)-8-sin-ethyl-8-isobutyl-8-azoniabicyclo-[3.2.1.]-octane iodide Endo-3-(2-phenyl-2-cyclohexen-1-carbonyloxy)-8-sin-propyl-8-methyl-8-azoniabicyclo-[3.2.1.]-octane iodide Endo-3-(2-phenyl-2-cyclohexen-1-carbonyloxy)-8-sin-propyl-8-ethyl-8-azoniabicyclo-[3.2.1.]-octane iodide Endo-3-(2-phenyl-2-cyclohexen-1-carbonyloxy)-8,8-dipropyl-8-azoniabicyclo-[3.2.1.]-octane iodide Endo-3-(2-phenyl-2-cyclohexen-1-carbonyloxy)-8-sin-propyl-8-isopropyl-8-azoniabicyclo-[3.2.1.]-octane iodide Endo-3-(2-phenyl-2-cyclohexen-1-carbonyloxy)-8-sin-propyl-8-n.butyl-8-azoniabicyclo-[3.2.1.]-octane iodide Endo-3-(2-phenyl-2-cyclohexen-1-carbonyloxy)-8-sin-propyl-8-isobutyl-8-azoniabyciclo-[3.2.1.]-octane iodide Endo-3-(2-phenyl-2-cyclohexen-1-carbonyloxy)-8,8-dimethyl-8-azoniabicyclo-[3.2.1.]-octane methylsulphate Endo-3-(2-phenyl-2-cyclohexen-1-carbonyloxy)-8-sin-methyl-8-ethyl-8-azoniabicyclo-[3.2.1.]-octane methylsulphate Endo-3-(2-phenyl-2-cyclohexen-1-carbonyloxy)-8-sin-isopropyl-8-methyl-8-azoniabicyclo-[3.2.1.]-octane methylsulphate Endo-3-(2-phenyl-2-cyclohexen-1-carbonyloxy)-8-sin-propyl-8-methyl-8-azoniabicyclo-[3.2.1.]-octane methylsulphate Endo-3-(2-phenyl-2-cyclohexen-1-carbonyloxy)-8-sin-isopropyl-8-methyl-8-azoniabicyclo-[3.2.1.]-octane bromide Endo-3-(2-phenyl-2-cyclohexen-1-carbonyloxy)-8-sin-isopropyl-8-methyl-8-azoniabicyclo-[3.2.1.]-octane bromide Endo-3-(2-phenyl-2-cyclohexen-1-carbonyloxy)-8-sin-ethyl-8-methyl-8-azoniabicyclo-[3.2.1.]-octane bromide Endo-3-(2-phenyl-2-cyclohexen-1-carbonyloxy)-8,8-diethyl-8-azoniabicyclo-3.2.1.]-octane bromide.

3. Composition for producing an anti-bronchospastic action comprising an effective amount of a compound of claim 1 and a pharmaceutically acceptable carrier or adjuvant.

4. Composition of claim 3, in a form suitable for administration by inhalation.

* * * * *

UNITED STATES PATENT AND TRADEMARK OFFICE
CERTIFICATE OF CORRECTION

PATENT NO. : 4,780,467

DATED : October 25, 1988

INVENTOR(S) : Turbanti et al

Page 1 of 4

It is certified that error appears in the above-identified patent and that said Letters Patent is hereby corrected as shown below:

```
Column 1 line 22 next to the structural formula insert --I--
Column 1 line 30 delete "1-2" and replace by --2-3--
Column 1 line 31 delete "2-3" and replace by --1-2--
Columns 5 and 6 amend Scheme I to read as on the attached sheet.
Column 9 left hand column of Table 1 amend the structural
formula to read as follows:
```

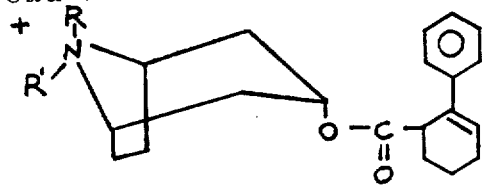

Signed and Sealed this

Eighteenth Day of June, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,780,467
DATED : October 25, 1988
INVENTOR(S) : Turbanti, et al It is certified that error appears in the above-identified patent and that said Letters Patent is hereby corrected as shown below:

Column 11 left hand column of Table 2 amend the structural formula to read as follows:

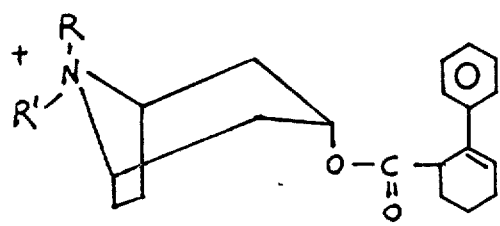

UNITED STATES PATENT AND TRADEMARK OFFICE
CERTIFICATE OF CORRECTION

PATENT NO. : 4,780,467
DATED : October 25, 1988
INVENTOR(S) : Turbanti et al

It is certified that error appears in the above identified patent and that said Letters Patent is hereby corrected as shown below:

Column 19 line 21 amend "di-ethyl-azoniabicyclo-[3.2.1.]-octane iodide" to read --di-ethyl-8-azoniabicyclo-[3.2.1.]-octane iodide--
Column 20 line 31 delete "azoniabicyclo-[3.2.1.]-octane iodide" and replace by --dipropyl-8-azoniabicyclo-[3.2.1]-octane iodide--
Column 22 line 6 delete "R'=" (first occurrence)
Column 22 line 35 delete "-8-sin-isopropyl"
Column 24 lines 1 through 10 delete the structural formula and replace by the following structure:

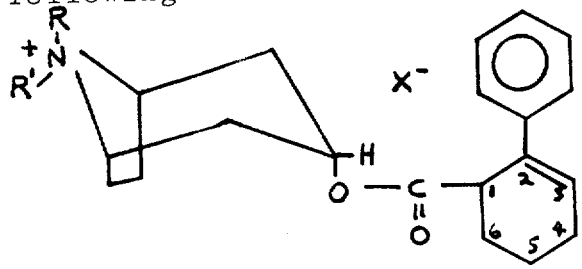

Column 24 line 31 delete "-8-sin-isopropyl"
Column 24 line 34 delete "8-ethyl" and replace by --8-methyl--
Column 24 line 39 delete "2-phenyl-1-cyclohexen-" and replace by --2-phenyl-2-cyclohexen- --
Column 24 line 42 delete "-8-" and replace by -- -8,8- --
Column 26 line 11 delete "8-methyl" and replace by --8-ethyl--